(12) United States Patent
Zegarelli

(10) Patent No.: US 8,113,837 B2
(45) Date of Patent: Feb. 14, 2012

(54) ORAL APPLIANCE FOR DELIVERING A MEDICAMENT

(76) Inventor: Peter John Zegarelli, Sleepy Hollow, NY (US)

( * ) Notice: Subject to any disclaimer, the term of this patent is extended or adjusted under 35 U.S.C. 154(b) by 0 days.

(21) Appl. No.: 11/986,727

(22) Filed: Nov. 26, 2007

(65) Prior Publication Data

US 2009/0136893 A1    May 28, 2009

(51) Int. Cl.
*A61C 5/00* (2006.01)

(52) U.S. Cl. .......................................... 433/215

(58) Field of Classification Search .............. 433/6, 37, 433/80, 215, 229, 217.1; 128/861, 862
See application file for complete search history.

(56) References Cited

U.S. PATENT DOCUMENTS

| | | | |
|---|---|---|---|
| 3,234,942 A | 2/1966 | Simor | |
| 3,339,547 A | 9/1967 | Drabowski | |
| 3,527,219 A * | 9/1970 | Greenberg | 433/25 |
| 3,536,069 A | 10/1970 | Gores at al | |
| 3,705,585 A | 12/1972 | Saffro | |
| RE28,667 E | 12/1975 | Gores et al. | |
| 4,173,219 A | 11/1979 | Lentine | |
| 4,173,505 A | 11/1979 | Jacobs | |
| 4,430,013 A | 2/1984 | Kaufman | |
| 5,323,787 A * | 6/1994 | Pratt | 128/862 |
| 5,575,654 A | 11/1996 | Fontenot | |
| 5,732,715 A | 3/1998 | Jacobs et al. | |
| 5,980,249 A | 11/1999 | Fontenot | |
| 5,985,249 A | 11/1999 | Fischer | |
| 6,030,213 A | 2/2000 | Trop | |
| 6,210,162 B1 | 4/2001 | Chishti et al. | |
| 6,217,606 B1 | 4/2001 | Portnoy et al. | |
| 6,247,930 B1 | 6/2001 | Chiang et al. | |
| 6,274,122 B1 | 8/2001 | McLaughlin | |
| 6,276,935 B1 | 8/2001 | Funt | |
| 6,319,510 B1 | 11/2001 | Yates | |
| 6,386,869 B1 | 5/2002 | Zegarelli | |
| 6,458,380 B1 | 10/2002 | Leaderman | |
| 6,471,511 B1 | 10/2002 | Chishti et al. | |
| 6,626,669 B2 | 9/2003 | Zegarelli | |
| 6,638,496 B2 | 10/2003 | McLaughlin | |
| 6,660,029 B2 | 12/2003 | VanSkiver et al. | |
| 6,896,519 B2 | 5/2005 | Chen | |
| 6,935,857 B1 * | 8/2005 | Farrell | 433/6 |
| 6,966,773 B2 | 11/2005 | Keller | |
| 6,984,128 B2 | 1/2006 | Breining et al. | |
| 7,029,690 B1 | 4/2006 | Wehrli | |
| 7,036,514 B2 | 5/2006 | Heck | |

(Continued)

FOREIGN PATENT DOCUMENTS

EP    1570803    2/2006

(Continued)

*Primary Examiner* — Cris L Rodriguez
*Assistant Examiner* — Eric Rosen
(74) *Attorney, Agent, or Firm* — Dilworth & Barrese, LLP; William D. Schmidt

(57) ABSTRACT

An oral appliance is provided for delivering a medicament to at least a portion of teeth and/or soft tissue areas inside a mouth, the oral appliance having an interior surface having a porous material disposed on at least a portion of the interior surface of the oral appliance, the porous material containing a medicament and the interior surface being formed to fit contours of at least the portion of the teeth and/or soft tissue areas inside the mouth and being capable of supporting and holding the porous material in contact with at least the portion of the teeth and/or soft tissue areas inside the mouth to deliver the medicament.

25 Claims, 7 Drawing Sheets

U.S. PATENT DOCUMENTS

| | | |
|---|---|---|
| 7,044,929 B2 | 5/2006 | VanSkiver |
| 7,055,530 B2 | 6/2006 | Husted |
| 7,059,858 B2 | 6/2006 | McLean |
| 7,063,532 B1 | 6/2006 | Jones et al. |
| 7,074,042 B2 | 7/2006 | Allred |
| 7,074,426 B2 | 7/2006 | Kochinke |
| 7,114,953 B1 | 10/2006 | Wagner |
| 7,134,874 B2 | 11/2006 | Chishti et al. |
| 7,160,111 B2 | 1/2007 | Baughman |
| 7,172,423 B2 | 2/2007 | Allred |
| 7,192,280 B2 | 3/2007 | Allred |
| 7,241,143 B2 | 7/2007 | Discko, Jr. et al. |
| 2003/0003421 A1 | 1/2003 | Bestenheider et al. |
| 2003/0205234 A1* | 11/2003 | Bardach et al. ............... 128/861 |
| 2003/0207227 A1 | 11/2003 | Abolfathi |
| 2004/0229185 A1 | 11/2004 | Knopp |
| 2004/0253562 A1 | 12/2004 | Knopp |
| 2005/0055118 A1 | 3/2005 | Nikolskiy et al. |
| 2005/0137109 A1 | 6/2005 | Quan et al. |
| 2005/0137110 A1 | 6/2005 | Scott et al. |
| 2005/0143274 A1 | 6/2005 | Ghosh et al. |
| 2007/0071693 A1 | 3/2007 | Kurihara et al. |
| 2007/0122360 A1 | 5/2007 | Oniki et al. |
| 2008/0044797 A1* | 2/2008 | Bardach et al. ............. 433/217.1 |

FOREIGN PATENT DOCUMENTS

| | | |
|---|---|---|
| MX | 2006006946 A | 8/2006 |
| WO | 00/19928 | 4/2000 |

\* cited by examiner

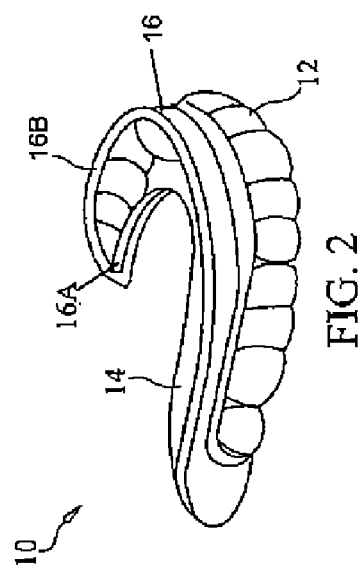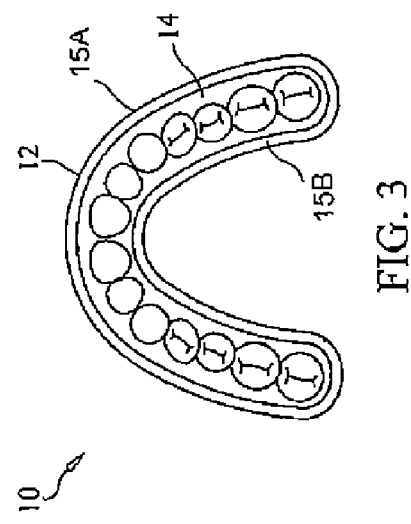

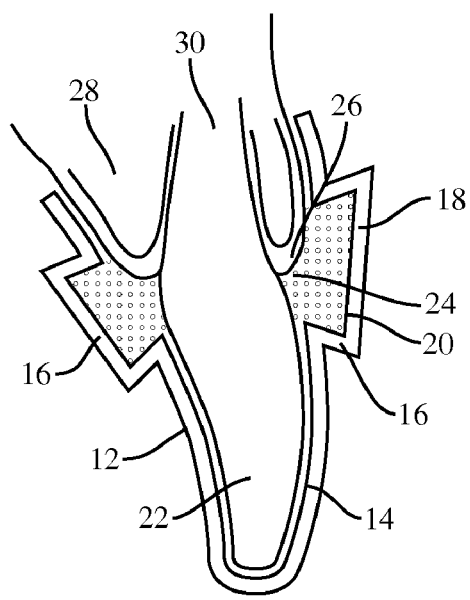
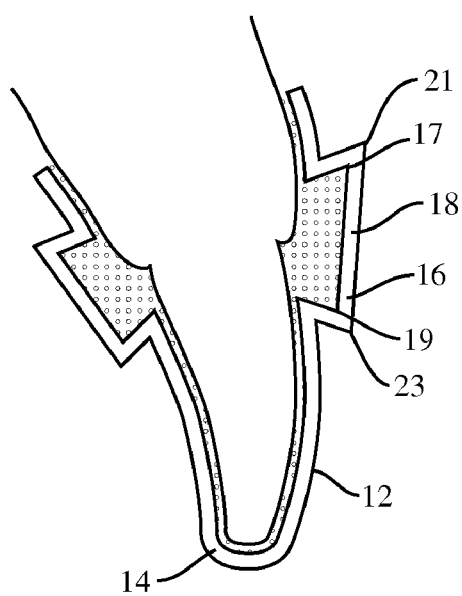
FIG. 5
FIG. 6

ORAL APPLIANCE FOR DELIVERING A MEDICAMENT

BACKGROUND

Medicaments may be delivered to patients by a variety of ways including oral, intravenous, intramuscular, inhalation, topical, rectal, subcutaneous or local routes of administration to treat the target site. The method of delivery chosen depends, among other things, upon the condition being treated, desired therapeutic concentration of the medicament and the duration of medicament concentration that must be maintained at the target site.

Recently, there has been considerable interest in delivering medicaments via the oral cavity (e.g., gums, buccal, and sublingual areas, etc.). Delivery to target sites of the oral cavity has several advantages. One advantage is that it allows localized treatment of the teeth, gums and other soft tissues. Another advantage is that the oral cavity has an extensive network of blood capillaries under the mucosa that is particularly suited to provide rapid and effective systemic absorption of systemic medicaments.

Delivery of medicaments to target sites in the oral cavity, unlike the intravenous (IV), intramuscular (IM), and subcutaneous (SC) routes, does not require sterilized hypodermic needles and does not raise concerns about the safe disposal of needles and accidental needle sticks.

Many, if not most, patients experience anxiety and exhibit symptoms of stress when faced with hypodermic injections via the IM, IV, or SC routes. Burning, edema, swelling, turgidity, hardness and soreness at the injection site can often occur.

Non-invasive delivery of medicaments to the oral cavity avoids these problems associated with injections. Non-invasive delivery of medicaments to the oral cavity also has the advantage of avoiding hepatic first pass metabolism, where enzymatic degradation within the gastrointestinal tract destroys certain medicaments. For example, therapeutic peptides such as insulin, erythropoietin, and human growth hormone do not survive the acidic milieu of the stomach and cannot be administered orally.

Many oral medicaments are commercially available for cosmetic and therapeutic use, which are delivered locally to the oral cavity. These medicaments are formulated as mouthwashes, rinses, toothpastes, dental gels, tooth powder, chewing gum, lozenges, strips and similar products to treat a variety of conditions including preventing dental calculus formation, dental caries, periodontitis and gingivitis, tooth whitening, as well as the elimination of halitosis. While these formulations provide some benefits, they often require a higher dose and do not stay at the target site long enough for adequate delivery of the medicament and are diluted away by saliva also decreasing effectiveness.

Oral appliances that allow non-invasive delivery of medicaments have been developed that have a reservoir to hold liquid medicaments to be delivered. These oral appliances can be universal sizes to generically fit adults or custom made for a precise fit to the teeth and gums of the individual patient. To whiten teeth, these oral appliances are becoming increasingly popular as over-the-counter tooth whitening systems or as part of a treatment plan from dental professionals.

Many oral appliances require the patient or dental professional to fill the reservoir with the liquid medicament. This can be costly and time consuming, and can be very messy with bulky dispensers requiring dexterity particularly when the patient is filling the oral appliance by himself/herself in the confines of their home. This leads to poor patient compliance and the failure of the treatment itself. Often the liquid medicament held by the oral appliance undesirably leaks out of the oral appliance and contacts off target areas of the mouth causing unwanted treatment of these non-targeted areas often with deleterious side effects such as burning, stinging and irritation and altered taste sensations. Sometimes medicament can leak out of the appliance and the patient will swallow the medicament into the gastro-intestinal tract—not a desirable outcome. This loss of medicament may lead to reduced efficacy in the treatment.

Based on the above, new oral appliances are needed that improve delivery of the medicament to the target site. Oral appliances that can be easily manufactured, are preloaded and pre-dosed with medicaments, which reduce unwanted leakage, that are easy and comfortable for the patient and are not limited to the confines of home are also needed.

SUMMARY

New oral appliances are provided that increase contact time of the medicament with the target site to improve delivery of the medicament. One advantage of the oral appliance is that, in various embodiments, it reduces or eliminates unwanted leakage of the medicament out of the oral appliance that can contact off target areas of the mouth causing unwanted burning, stinging and irritation and taste alterations. Another advantage of the oral appliance is that, in various embodiments, it is pre-filled with the medicament at a specific dose and does not require the patient or dental professional to fill it with the liquid medicament, saving time and avoiding the mess. Still another advantage of the oral appliance is that, in various embodiments, it can be easily manufactured and is comfortable for the patient to use and transportable. Still yet another advantage, in various embodiments, is that lower doses of the medicament may be used because better contact with the target site is achieved over time and the medicament is not diluted away by saliva.

In one embodiment, an oral appliance is provided for delivering a medicament to at least a portion of teeth and/or soft tissue areas inside a mouth, the oral appliance comprising an interior surface having a porous material disposed on at least a portion of the interior surface of the oral appliance, the porous material containing a medicament and the interior surface being formed to fit contours of at least the portion of the teeth and/or soft tissue areas inside the mouth and being capable of supporting and holding the porous material in contact with at least the portion of the teeth and/or soft tissue areas inside the mouth to deliver the medicament.

In another embodiment, an oral appliance is provided for delivering a medicament to at least a portion of teeth and/or soft tissue areas inside a mouth, the oral appliance comprising an interior surface having one or more recesses and/or projections and having a porous material disposed on at least a portion of the interior surface of the oral appliance, the porous material containing a medicament and the interior surface being formed to fit contours of at least the portion of the teeth and/or soft tissue areas inside the mouth and being capable of supporting and holding the porous material in contact with at least the portion of the teeth and/or soft tissue areas inside the mouth to deliver the medicament, wherein the porous materials contains complementary recesses and/or projections that fit into the interior surface of the oral appliance.

In an exemplary embodiment, a method of delivering a medicament to at least a portion of teeth and/or soft tissue areas inside a mouth is provided, the method comprising: providing an oral appliance comprising an interior surface and a porous material disposed on at least the portion of the interior surface of the oral appliance and containing a medicament, the interior surface being formed to fit contours of at least the portion of the teeth and/or soft tissue areas inside the mouth and being capable of holding the porous material in contact with at least the portion of the teeth and/or soft tissue areas inside the mouth; and covering at least the portion of the teeth and/or soft tissue areas inside the mouth with the oral appliance supporting the porous material so that the porous material contacts at least the portion of the teeth and/or soft tissue areas inside the mouth to deliver the medicament.

In another exemplary embodiment, a computer-implemented method is provided for creating a treatment plan for delivering a medicament to at least a portion of the teeth and/or soft tissue areas inside the mouth, the computer-implemented method comprisingly: receiving an initial digital data set representing at least a portion of the teeth and/or soft tissue areas inside the mouth by scanning at least the portion of the teeth and/or soft tissue areas inside the mouth or a physical model or impression thereof; storing the initial digital data set in a database; generating a series of treatment plans to deliver the medicament to at least a portion of the teeth and/or soft tissue areas inside the mouth based on the stored initial digital data set, and constructing a series of oral appliances based on the stored initial digital data set, each appliance capable of delivering a medicament to at least a portion of the teeth and/or soft tissue areas inside the mouth.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 2 illustrates an enlarged side view of an embodiment of the oral appliance without the teeth and/or soft tissue inserted into the oral appliance.

FIG. 3 illustrates an enlarged interior view of an embodiment of the oral appliance.

FIG. 5 illustrates an enlarged side cross sectional view of the tooth and soft tissue areas of the mouth having an embodiment of the porous material and oral appliance disposed on a portion of the teeth and soft tissue area.

FIG. 6 illustrates an enlarged side cross sectional view of an embodiment of the oral appliance with an outline of the tooth and soft tissue areas. The outer shell encompasses the porous material. The porous material has a plurality of recesses and projections that fit into mating pairs of the recesses and projection of the oral appliance so that the porous material locks into place. In this illustration, the porous material once applied contacts the tooth and the gums.

Figure 1:
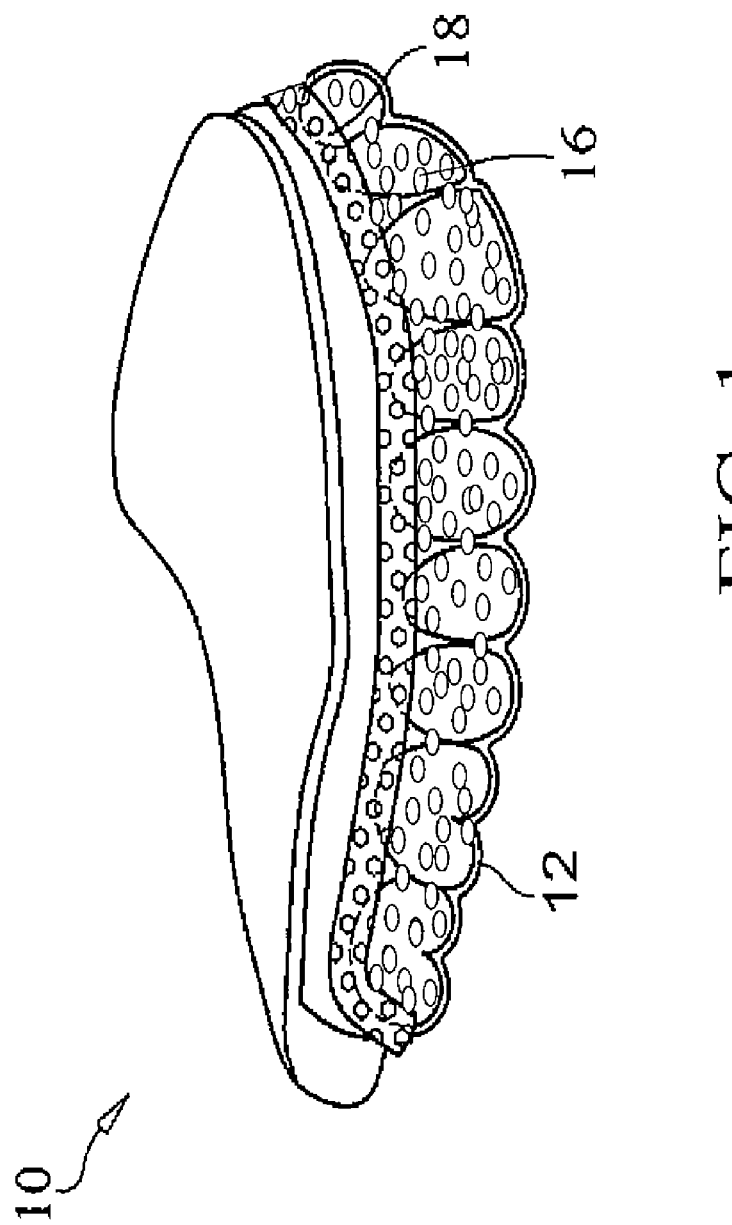
FIG. 1 illustrates an enlarged side view of an embodiment of the oral appliance covering the teeth and/or soft tissue areas of a patient. The oral appliance has a porous material disposed in its cargo area.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a medicament" includes one, two, three or more medicaments.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents which may be included within the invention as defined by the appended claims.

The headings below are not meant to limit the disclosure in any way; embodiments under any one heading may be used in conjunction with embodiments under any other heading.

New oral appliances are provided that increase contact time of the medicament with the target site to improve delivery of the medicament. One advantage of the oral appliance is that, in various embodiments, it reduces or eliminates unwanted leaks of the medicament out of the oral appliance that can contact off target areas of the teeth and soft tissue causing unwanted burning, stinging and irritation and taste alterations. Another advantage of the oral appliance is that, in various embodiments, it is pre-filled and dosed with the medicament and does not require the patient or dental professional to fill it with the liquid medicament, saving time and avoiding the mess and inaccurate dosing by the patient. Still another advantage of the oral appliance is that, in various embodiments, it can be easily manufactured and is comfortable for the patient to use.

In one embodiment, an oral appliance is provided for delivering a medicament to at least a portion of teeth and/or soft tissue areas inside a mouth, the oral appliance comprising an interior surface having a porous material disposed on at least a portion of the interior surface of the oral appliance, the porous material containing a medicament and the interior surface being formed to fit contours of at least the portion of the teeth and/or soft tissue areas inside the mouth and being capable of supporting and holding the porous material in contact with at least the portion of the teeth and/or soft tissue areas inside the mouth to deliver the medicament.

Oral Appliance

Referring to FIG. 1, an enlarged side view of an embodiment of the oral appliance 10 is illustrated, which has a non-porous exterior surface 12. The interior surface contacts one or more teeth and/or soft tissue areas of a patient. In this view the interior surface is abutting the teeth and soft tissue. Oral appliances include, but are not limited to, oral trays, oral holders, oral covers, or the like that are designed to be placed within the oral cavity. The interior surface of the oral appliance contains a cargo area, the exterior surface of the cargo area is shown as 16 and a porous material 18 that fits within the cargo area of the interior surface of the oral appliance via mating pair (e.g., keystone). The porous material contains a medicament and the porous material contacts and extends over the teeth as indicated by the open circles. Unlike orthodontic appliances, the present oral appliance is not designed to move teeth.

Referring to FIG. 2, an enlarged interior view of an embodiment of the oral appliance 10 is illustrated, which has a non-porous exterior surface 12 and an interior surface 14 that receives one or more teeth and/or soft tissue areas of a patient. The interior surface of the oral appliance contains a cargo area that is capable of receiving and holding a porous material that fits within the cargo area of the interior surface of the oral appliance. The cargo area can be contiguous with the oral appliance. The exterior surface of the cargo area is shown as 16. 16B illustrates a front interior surface of the cargo area disposed above the labial surface of the anterior teeth and 16A illustrates a back interior surface of the cargo area disposed above the lingual surface of the posterior teeth. In this illustrated embodiment, treatment of the anterior and posterior teeth can occur simultaneously. For example, when treating gum disease, the cargo area will allow, in various embodiments, treatment of both the anterior and posterior gums simultaneously. In various embodiments, when whitening teeth, if the porous material containing the bleaching agent is held in the cargo area and contacts the labial, lingual and occlusal or incisal portions of the teeth, the bleaching agent can now whiten both the front and back portions of the teeth providing an additional whitening benefit.

Referring to FIG. 3, an enlarged interior view of an embodiment of the oral appliance 10 is illustrated, which has anon-porous exterior surface and an interior surface 14 that receives one or more teeth and/or soft tissue areas of a patient. The interior surface of the oral appliance contains a cargo area, which is capable of receiving and holding a porous material that fits within the cargo area of the interior surface of the oral appliance. Shown is one cargo area extending from the labial aspect 15A to the lingual aspect 15B.

In various embodiments, oral appliances can be manufactured by, for example, taking an impression of the patient's teeth and/or soft tissue areas of a patient, which registers all teeth surfaces plus soft tissue areas including the gingival margin. A stone or acrylic cast is promptly made of the impression. To add one or more cargo areas to the oral appliance, the cast is modified typically by building a layer of rigid material on the stone or acrylic cast corresponding to the specific teeth and/or soft tissue areas to be treated. A dental appliance is then vacuum formed from the modified cast. Once formed, the dental appliance can be trimmed according to the area that is to be treated, for example, just below the muco-gingival margin on the buccal aspect and trimmed similarly on the lingual aspect.

In various embodiments, depending on the area to be treated, enough material should be left to assure that the oral appliance covers all teeth within about 1 mm of the gingival border upon finishing and beveling the appliance.

All appliance edges can be smoothed so that the lip and tongue will not feel an edge prominence to provide additional comfort to the patient. The resulting appliance, in one exemplary embodiment, provides a perfect fit of the patient's teeth with one or more cargo areas on the interior surface (e.g., grooves, spaces, gaps, indentations, or area that can hold the porous material) located where the rigid material was placed on the cast.

In various embodiments, the oral appliance may be a hard appliance, which is custom fitted to the patient's dental arches. In another embodiment, the oral appliance may be a rigid custom dental appliance that is an "oversized" rigid custom dental appliance. The fabrication of rigid, custom dental appliances entails fabricating stone or acrylic models of the patient's dental arch impressions, and heating, and vacuum-forming a thermoplastic sheet to correspond to the stone or acrylic models of a patient's dental arches. Thermoplastic films are sold in rigid or semi rigid sheets, and are available in various sizes and thickness. The dental laboratory fabrication technique for the oversized rigid dental appliance involves augmenting the facial surfaces of the teeth on the stone or acrylic models with materials such as die spacer or light cured acrylics. Next, thermoplastic sheeting is heated and subsequently vacuum formed around the augmented stone or acrylic models of the dental arch. The net effect of this method results in an "oversized" rigid custom dental appliance. Thus the oral appliance, in various embodiments, can be made in a larger size to accommodate for a thicker porous material. The entire oral appliance and components, in various embodiments, may be disposable—used once and thrown away; in this embodiment the patient may receive, for example, a 30 day supply of 30 pre-filled and dosed appliances each to be used once and then thrown away. In other embodiments, one or more component parts of the oral appliance can be re-used.

There are many methods of forming and shaping the oral appliance. One economical method of molding or forming the oral appliance is through injection molding. Injection molding is generally the forming or molding method of choice for thermoplastics. Injection molding generally requires the manufacture of a hollow cavity mold of any desired appliance. The hollow cavity is then filled under pressure with molten plastic and allowed to cool, followed by removal of the formed appliance from the mold.

In another embodiment, the oral appliance can be economically manufactured via compression molding. Typically, compression molding involves manufacture of a mold. The thermoplastic polymer is introduced into the mold, followed with heat and mechanical pressure the polymer is compressed and cooled into a desired shape. Other methods of forming or molding the oral appliance may also include thermoforming molding, blow molding, extrusion molding, transfer molding, reaction injection molding, or any like molding or forming method and the present application is not limited to one particular method of making the oral appliance and in general, any polymer that is capable of being formed or shaped into an oral appliance by the use of heat and/or pressure is within the scope of this application.

A suitable polymer to make the oral appliance can be one with a low melting point that is generally non-toxic or biocompatible and one that readily can incorporate the porous material during the compounding process. Many plastics and plastic combinations are suitable to make the oral appliance. A few examples of possible plastics include: polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters, urea-formaldehyde, or combinations thereof any like plastics. The oral appliance may be made from non-biodegradable polymers including ethylene vinyl acetate, poly(meth)acrylic acid, polyamides, copolymers and mixtures thereof. The characteristics or properties of these thermally formable plastics or polymers may be optionally modified by the use of plasticizers or any durometer adjusting substance. A plasticizer may be added to adjust the final properties and characteristics favorably, such as to make the plastic or polymer softer or more pliable. Typically, the oral appliance comprises non-porous material and is disposable.

One particularly preferred oral appliance is described in U.S. Pat. Nos. 6,386,869 and 6,626,669 issued to Dr. Zegarelli for "Oral therapeutic Delivery Appliance." The entire disclosures of these patents are herein incorporated by reference into this disclosure.

In one embodiment, the interior surface of the oral appliance is formed from a hard thermoplastic sheet material molded to correspond to the contours and receive at least the portion of the teeth and/or soft tissue areas inside the mouth up to and including muco-buccal folds, hard and soft palates, lining mucosa, attached gingival tissue, and/or the mouth floor and the porous material is supported and held within a cargo area of the interior surface of the thermoplastic material of the oral appliance.

The soft tissue of the inside of the mouth, includes but is not limited to any soft tissue adjacent or between the teeth, including but not limited to the papilla, tissue of the upper and lower dental arches, marginal gingiva, gingival sulcus, interdental gingiva, gingival gum structure on lingual and buccal surfaces up to and including the muco-gingival junction and/or the upper palate and the floor of the mouth. In various embodiments, the soft tissue area includes the muco-buccal folds, hard and soft palates, lining mucosa, and/or attached gingival tissue. In various embodiments, the oral appliance receives one or more teeth including one or more molars, premolars, incisors, cuspids, tooth implant, or combination or portions thereof.

In another embodiment, the oral appliance comprises titanium dioxide disposed throughout the thermoplastic material. The titanium dioxide, or other ionically charged materials, will give the oral appliance a generally negative charge and plaque (having a generally positive charge) will be attracted to it. In this way, when the appliance is removed from the oral cavity, some plaque will be removed with it leading to the prevention and/or reduction of dental disease.

The dimensions of the oral appliance, among other things, will depend on the target treatment site and whether local or systemic delivery of the medicament is required. The oral appliance can be adapted to any size and shape to receive at least a portion of the teeth and/or soft tissue areas inside the mouth to deliver the medicament. For example, the oral appliance is designed to contour, support and hold the porous material and, in various embodiments, extends to at least to the muco-gingival junction, or at least 2 mm to 5 mm buccally or lingually beyond a gingival margin, or contact all or substantially all of one or more teeth and/or soft tissue areas inside the mouth and adjacent buccal and lingual soft tissue areas.

In various embodiments, the oral appliance has a thickness of from about 0.06 inches to about 0.2 inches, a depth of at least about 1 mm to about 5 mm and a width of from about 1 mm to about 10 mm. In various embodiments, the oral appliance will be larger, smaller or the same size as the porous material.

The oral appliance comprises on its interior surface one or more cargo areas to hold and/or support the porous material. A cargo area includes, but is not limited to, grooves, spaces, gaps, indentations, punches, or one or more areas that can hold one or more porous materials. The cargo area can hold the porous material and some liquid medicament in the case where the porous material is hypo-saturated, saturated or supersaturated with liquid medicament. The dimensions of the cargo area, among other things, will depend on the target site and whether local or systemic delivery is required. The cargo area can be adapted to any size and shape cargo to maximize treatment. For example, the cargo area can correspond to the gingival margin and sulcus and be disposed adjacent to this area for treatment of periodontal disease so that the porous material and medicament contacts the gingival margin and sulcus for direct localized treatment of this area. The cargo area may also encompass partly or wholly the teeth for the treatment of caries or tooth bleaching.

In various embodiments, the cargo area is adapted to receive the porous material and may have a depth of from about 1 mm to about 5 mm and a width of from about 1 mm to about 5 mm. The one or more cargo areas can be discontinuous and disposed at various portions throughout the interior surface of the oral appliance or continuously disposed throughout the interior surface of the oral appliance.

In various embodiments, the oral appliance and/or cargo area comprises one or more recesses and/or projections so that corresponding recesses and/or projections from the porous material can mate and lock the porous material to the oral appliance and/or cargo area. Various means can hold or retain the porous material to the oral appliance and/or cargo area including, but not limited to, adhesive, keystone mating pairs, tracks, clips, ribs, snap fit members, recesses, projections, male-female mating pairs, Velcro, tape, or combinations thereof or the like. In various embodiments, the oral appliance and/or cargo area includes projections and/or recesses that may be any size and shape (e.g., straight, flat-sided shape, an elliptical shape, bi-concave shape, square shape, or any other protruding shape), which allows the porous material to physically lock in place in the oral appliance and/or cargo area.

Porous Material

The porous material can be any material that can hold and release the medicament. In various embodiments, the porous material has the medicament coated on or imbedded in it. The medicament may be present in layers throughout the porous material. In various embodiments, the porous material may be saturated with the medicament to provide the patient with a bolus dose of the medicament upon insertion of the appliance and compression of the porous material against the teeth and/or soft tissue.

In various embodiments, the porous material can hold some or all of the liquid medicament when the porous material is hypo-saturated, saturated, or supersaturated with liquid medicament.

The porous material is disposed at one or more locations of the interior surface of the appliance and is formed to fit contours of at least the portion of the teeth and/or soft tissue areas inside the mouth. In various embodiments, the porous material comprises a sponge or foam material that contains cells that hold the medicament and provide comfort to the patient (e g., cushion zone).

The sponge or foam can be produced by methods known to those of ordinary skill in the art. Depending on the starting material employed, in the simplest case a foam can be obtained by blowing in, by beating, shaking, spraying or stirring the material in the relevant gas atmosphere. In the case of polymers, the foam structure arises due to chemical reactions. Thus, polyurethanes are foamed by adding blowing agents, which decompose, at a particular temperature during the processing to form a gas, or by adding liquid solvents during the polymerization. The foaming takes place either on leaving the extrusion die, that is to say following the extrusion or injection molding or in open moulds. Curing takes place under the conditions characteristic of the particular chemical compound of the carrier material.

The porous material may be made from, for example, polymers, such as, for example, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyvinylpyrrolidone or a combination thereof.

The porous material, in various embodiments, may comprise non-biodegradable polymers, or biodegradable polymers, or a combination thereof. Examples of non-biodegradable polymers include, but are not limited to, ethylene vinyl acetate, poly(meth)acrylic acid, polyamides, copolymers and mixtures thereof. Examples of biodegradable polymers include synthetic polymers such as polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

The porous material can comprise orally soluble or insoluble polymers. For example, the porous material may be designed to be insoluble in the oral environment, yet still release the medicament that is coated on or internally imbedded in the porous material. Alternatively, the porous material could be designed such that the polymer and one or more medicaments could dissolve in the oral environment. Such orally dissolvable porous material would release imbedded medicaments as the polymer is dissolved away by the flow of saliva. Various polymers whether soluble, insoluble, semi-soluble or combinations of these may be used to create a porous material with specific active ingredient releasing capabilities. Many plastics and plastic combinations are suitable for this application. A few examples of possible plastics include: polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters, urea-formaldehyde, or any like plastics.

Like the oral appliance, the porous material may comprise a plasticizer to adjust the final properties and characteristics favorably, such as to make the plastic softer or more pliable. A plasticizer may also be used to facilitate the metered release of medicament. A plasticizer may be chosen such that it will readily dissolve in saliva along with the medicament. A plasticizer of this type would thus aid in the release of the medicament. Therefore, the oral release could be adjusted or metered at different rates by adding different quantities or types of plasticizers to the porous material. Many plasticizers would alter the polymeric properties to a desired plasticity and/or aid in the release of the medicament. A few examples of possible plasticizers includes: mineral oil, triethyl citrate, acetyltriethyl citrate, lauric acid, modified vegetable oils, diacetylated monoglycerides, castor oil, sucrose diacetate hexaisobutyrate, triacetin, glycerin, liquid polyethylene glycols, liquid poly propylene glycols, propylene glycol, dimethyl phthalate, diethyl phthalate, dipropyl phthlate, dibutyl phthalate, dioctyl phthalate, polysorbates or any like or useful plasticizer.

In one embodiment the porous material may comprise a backing material (e.g., a closed cell plastic backing material) to minimize elution of the medicament from the oral appliance, into the oral cavity to minimize ingestion by the patient and/or irritation of the oral cavity tissues. The porous material can be constructed to increase release of the medicament to give a bolus dose or the porous material may be designed to prevent medicament from spilling out of the porous material and allow the medicament to pass through the porous material over time to obtain a sustained release profile. In other words, in various embodiments, the porous material may have an internal structural spacing sized relative to the viscosity of the medicament to absorb and allow the composition to pass there through to achieve the desired medicament release profile (e.g., immediate release, bolus release, sustained or controlled release, etc.).

In another embodiment, the porous material comprises titanium dioxide disposed throughout it. The titanium dioxide, or other ionically charged materials, will give the oral appliance a generally negative charge and plaque (having a generally positive charge) will be attracted to it. In this way, when the porous material is removed from the oral cavity, some plaque will be removed with it leading to the prevention and/or reduction of tooth decay.

An example of a porous material suitable for use includes, but is not limited to, sponge, foam or strip containing closed cell polyolefin foam sold by the Voltek division of Sekisui America Corporation of Lawrence, Mass. under the tradename Volora™ which is from about 1/32 to 1/8 inches in thickness. A closed cell material may also comprise of a flexible polymeric material.

Another example of a porous material suitable for use includes, but is not limited to, sponge or foam or strip containing open cell polyethylene foam sold by the Sentinel Foam Products division of Packaging Industries Group, Inc. of Hyannis, Mass. under the tradename Opcell which is from about 1/16 to 3/8 inches in thickness. Other open cell foam useful herein includes hydrophilic open foam materials such as hydrogel polymers (e.g., Medicell™ foam available from Hydromer, Inc. Branchburg, N.J.). Open cell foam may also be hydrophilic open foam material impregnated with agents to impart high absorption of fluids, such as polyurethane or polyvinylpyrrolidone chemically impregnated with various agents.

The dimensions of the porous material, among other things, will depend on the target treatment site and whether local or systemic delivery of the medicament is required as well as the type of medicament release profile to achieve. The porous material can be adapted to any size and shape to attached to the cargo area and receive at least a portion of the teeth and/or soft tissue areas inside the mouth to deliver the medicament. For example, the porous material may, in various embodiments, extend to at least the muco-gingival junction, or at least 2 mm to 5 mm buccally or lingually beyond a gingival margin, or contact all or substantially all of one or more teeth and/or soft tissue areas inside the mouth and adjacent buccal and lingual soft tissue areas. In various embodiments, the porous material contacts all or substantially all of one or more teeth and/or soft tissue areas inside the mouth. In various embodiments, the porous material contacts the soft tissue and teeth at or near a gingival margin or sulcus.

In various embodiments, the porous material has a thickness of from about 0.06 inches to about 0.2 inches, a depth of at least about 1 mm to about 5 mm and a width of from about 1 mm to about 10 mm. In various embodiments, the porous material will be smaller than the oral appliance. The porous material is held and supported by the oral appliance and/or cargo area. Thus, in various embodiments, no adhesive is required to hold the porous material in place.

It should be understood by those of ordinary skill in the art that the porous material may be contiguous with the interior surface of the oral appliance or only disposed on certain portions of the interior surface of the oral appliance or, in other embodiments, the porous material may protrude out from the interior surface of the oral appliance to contact the teeth and/or soft tissue areas. Thus when inserted the porous material will be squeezed, releasing a bolus dose to the teeth and/or soft tissues. This all depends on the target site and whether local or systemic action of the medicament is desired.

In various embodiments, the porous material comprises one or recesses and/or projections that correspond to the recesses and/or projections from the oral appliance and/or cargo area. Various means can hold or retain the porous material to the oral appliance and/or cargo area including, but not limited to, adhesive, tracks, clips, ribs, snap fit members, recesses, projections, keystone mating pairs, male-female mating pairs, Velcro, tape, or combinations thereof or the like.

If an adhesive layer is used on the porous material, it may be composed of a bioadhesive, mucoadhesive and/or biocompatible pressure sensitive material. Exemplary adhesive materials include polyurethanes; acrylic or methacrylic resins, and their copolymers with other compounds; polyoxyethylenes; polyanhydrides; natural or synthetic rubbers; polyvinylacetate; poly(vinylpyrrolidone); cellulose derivatives; hyaluronic acid; chitosan; natural gums; and so forth. The adhesive may also include tackifiers, stabilizers or plasticizers (e.g., triethyl citrate, dibutylphthalate, diethylphthalate, acetyltriethyl citrate, tributyl citrate, acetyltetrabutyl citrate, triacetin, polyethylene glycol, castor oil), or a combination thereof.

In various embodiments, an adhesive is not used and the porous material is held in place by physical locks (e.g., keystone mating pairs) or friction or force from the oral appliance, which will snuggly fit the teeth and/or soft tissue areas inside the mouth.

In various embodiments, the porous material includes projections and/or recesses that may be any size and shape (e.g., straight, flat-sided shape, an elliptical shape, bi-concave shape, square shape, or any other protruding shape), which allows the porous material to stay in place in the oral appliance and/or cargo area.

Figure 4:
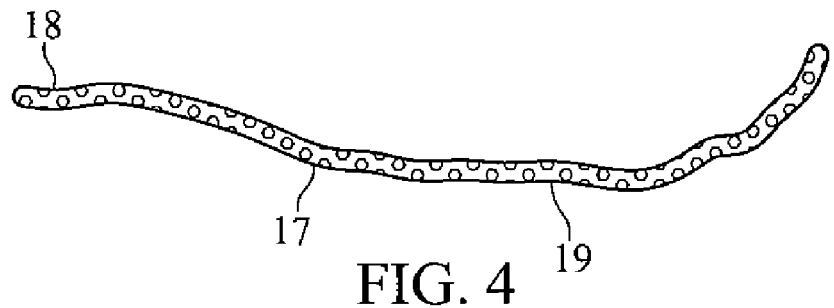
FIG. 4 illustrates an enlarged side view of an embodiment of the porous material having recesses and projections that fit into the oral appliance.
Figure 4A:
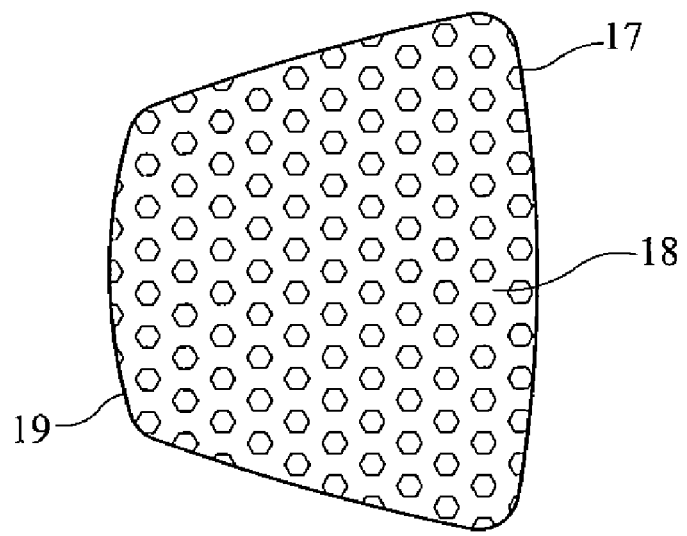
FIG. 4A illustrates a cross-sectional view of the porous material.

Referring to FIG. 4, it illustrates an enlarged side view of an embodiment of the porous material 18 having mating pairs 17 and 19 that fit into the oral appliance. Although the porous material is shown as a single continuous piece, it will be understood that the porous material can be discrete pieces disposed throughout the cargo area or oral appliance. FIG. 4A illustrates a cross-sectional view of the porous material 18 in the keystone embodiment. 19 shows a part of the porous material of the keystone contacting the portion of the teeth and/or soft tissues and 17 is that part of the porous material abutting the interior surface of the oral appliance.

FIG. 5 illustrates an enlarged side cross sectional view of an embodiment of the oral appliance having a porous material 18 contacting the tooth 22, soft tissue around the tooth root 26 and soft tissue around the bone 28, gingival area 26, and sulcus area 24 of the inside of the mouth. The tooth root is shown as 30. The oral appliance has an exterior surface 12 and interior surface 14 that contours the tooth 22, soft tissue around the tooth root 26, and soft tissue around the bone 28, gingival area 26, and sulcus area 24 of the inside of the mouth. Disposed on an interior surface of the oral appliance in the cargo area 16 is the porous material 18 which contacts the tooth 22, soft tissue around the tooth root 26, and soft tissue around the bone 28, gingival area 26, and sulcus area 24 of the inside of the mouth to deliver the medicament thereto. The oral appliance holds and supports the porous material at one or more target sites to deliver the medicament. The porous material locks into the oral appliance at keystone mating pair 20 so that the porous material stays in place. In this illustration, the oral appliance is trimmed approximating the mucogingival junction on the labial aspect and along the palate on the lingual aspect.

FIG. 6 illustrates an enlarged side cross sectional view of an embodiment of the oral appliance loaded with the porous material. The exterior surface of the oral appliance is shown as 12. Interior surface 14 of the oral appliance is capable of receiving the porous material 18 and has keystone shaped mating pairs 17 and 19, which insert into (e.g., lock, snap, etc.) corresponding keystone shaped mating pairs 21 and 23 respectively. These mating pairs keep the porous material in place in the cargo area 16 of the oral appliance. In this embodiment, the porous material may comprise two or more different types of medicaments disposed on or in different areas of the porous material that are adjacent to the target treatment site of the teeth and/or soft tissue areas. One or more medicaments (e.g., can be an antimicrobial, analgesic, etc.) can be disposed by or adjacent to the gum area shown between 17 and 19 to treat this area. The other medicament can be disposed adjacent to a second different treatment site adjacent to area 14 where the medicament can be, for example, be an anticaries agent, tooth de-sensitizing agent, bleaching agent or other medicament designed to treat the teeth. In this way, the oral appliance can treat different areas of the teeth and soft tissue simultaneously if needed. Thus, the patient can have his/her teeth whitened at the same time as having the periodontal disease treated.

Medicaments

The porous material contains one or more medicaments coated or layered on it or impregnated within it at the same or different areas. In various embodiments, some areas of the porous material do not contain one or more medicaments, and the porous material may function to hold or lock a portion of the porous material in place so that other portions of the porous material can contact the appropriate target site. Thus, in some embodiments, the porous material may contain one or more medicaments disposed in or on it throughout the whole porous material. In other embodiments, one or more portions of the porous material do not contain any medicament disposed in or on it. The term "medicament" as used herein is generally meant to refer to any substance that alters the physiology of a patient. The term "medicament" may be used interchangeably herein with the terms "drug" "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments.

The medicament may be in powder, liquid, solid, solution, or suspension (e.g., gel) form and disposed on or impregnated in the porous material. This may occur during manufacture of the porous material or it may occur after the porous material is made. For example, on the core porous material, the medicament may be layered by solution or suspension layering or powder layering techniques. In solution or suspension layering, the medicament and any inactive ingredients (excipients, binders, etc.) are suspended or dissolved in water or an organic solvent. The resulting liquid is sprayed onto the outside of porous material to make the porous material have the desired potency. Solution or suspension layering may be conducted using a wide variety of process techniques, for example, by fluidized bed, Wurster bottom spray techniques, or the like. When the desired potency has been achieved, the porous material is dried to the desired residual moisture content. Powdered layering involves the application of a dry powder to the porous material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the porous material while applying the dry powder until the desired potency is achieved. When the desired potency has been achieved, the porous material may be dried to the desired moisture content.

In various embodiments, the medicament may be encapsulated in a lipid bilayer and then impregnated, coated or layered on the porous material. In various embodiments, the medicament can be micro-encapsulated into a carrier having a positive or negative charge, such as for example, a novasome® (available from IGI) to increase absorption of the medicament or cause it to have sustain release properties to release the medicament over hours (e.g., 1-24 hours or longer). The novasome® can be made using amphiphiles, which include a variety of fatty alcohols and acids to give the medicament the desired charge and release property.

In various embodiments, medicaments can now be used at lower doses as the porous material improves contact with the target treatment area(s) of the teeth and/or soft tissue. Thus, less dose of the medicament can be used because more effective concentration of medicament at the one or more target sites is achieved over time.

Examples of medicaments include, but are not limited to, anti-inflammatory agents, anti-infective agents (e.g., antiviral, antibacterial, antifungal agents, etc.), tissue and bone growth factors, pain management medication (e.g., analgesics, anesthetics, etc.) antineoplastic agents, tooth whitening agents, breath fresheners, anticalculus agents, antineoplastic agents, oral dermatologics, selective H-2 antagonists, anticaries agents, nutrients, vitamins, minerals, herbal products, or mixtures thereof.

The medicament may be a systemic medicament such as thyroid drug, e.g., anti-thyroid agents or thyrostatic substances that are compounds useful for the treatment of thyroid diseases, including hormones such as thyroxine (T4), triiodothyronine (T3); propylthiouracil; methimazole; and so forth.

In various embodiments, the porous material may contain more than one medicament. However, in another embodiment, combination therapy will involve use of a single safe and effective amount of the medicament. For example the method may further comprise subsequently administering one or more additional oral appliances, each containing a medicament that is different from the medicament contained in the earlier oral appliance. In this way, a series of customized treatment regimens can be provided to the patient. This provides for a "mix and match" medicament regimen with dose adjustment capability and provides the added advantage of allowing the health professional complete control to administer only those medicaments at the desired strength believed to be appropriate for the disease or condition being treated.

The amount of medicament contained within the porous material, will vary widely depending on the effective dosage required and rate of release from the porous material and the length of the desired delivery interval. The dosage administered to the patient can be single or multiple doses and will vary depending upon a variety of factors, including the agent's pharmacokinetic properties, patient conditions and characteristics (sex, age, body weight, health, size, etc.), extent of symptoms, concurrent treatments, frequency of treatment and the effect desired. These factors can readily be determined by those of ordinary skill in the art.

In various embodiments, the porous material is designed to release the medicament as a bolus dose of the medicament, a single dose of the medicament, or multiple doses of the medicament all preloaded with a specific dosage at the manufacturing facility.

Anti-inflammatory agents are of particular interest as it is believed that they serve not only to reduce inflammation but, in doing so, can also have a variety of other beneficial effects that may eliminate the need for or minimize the amount of additional medicaments. For example, if a patient is suffering from pain and inflammation, administration of an anti-inflammatory agent will alleviate inflammation and the tissue, once back to normal may no longer exert pressure on nerves and thus the need for additional pain medication may be minimized or eliminated entirely.

Suitable anti-inflammatory agents to treat and reduce inflammation include both steroidal and non-steroidal anti-inflammatories. Exemplary anti-inflammatory agents include by way of example and not limitation, alclofenac; alclometasone dipropionate; algestone acetonide; alendronate sodium; alpha amylase; amcinafal; amcinafide; amcinonide; amfenac sodium; amiprilose hydrochloride; anakinra; anirolac; anitrazafen; apazone; balsalazide disodium; beclomethasone diproprionate; bendazac; benoxaprofen; benzydamine hydrochloride; betamethasone; bromelains; broperamole; budesonide; carprofen; cicloprofen; cintazone; cliprofen; clobetasol propionate; clobetasone butyrate; clopirac; cloticasone propionate; cormethasone acetate; cortisone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; fludrocortisone; flufenamic acid; flumizole; flunisolide acetate; flunixin; flunixin meglumine; fluocinonide; fluocinolone acetonide; fluocortin butyl; fluorometholone acetate; fluquazone; flurandrenolide; flurbiprofen; fluretofen; fluticasone propionate; furaprofen; furobufen; halcinonide; halobetasol propionate; halopredone acetate; hydrocortisone; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisone dibutyrate; medrysone; mefenamic acid; mesalamine; meseclazone; methylprednisolone suleptanate; momifilumate; nabumetone; naproxen; naproxen sodium; naproxol; nimazone; nilutamide; olsalazine sodium; orgotein; orpanoxin; oxaprozin; oxyphenbutazone; pamidronate disodium; paramethasone; paranyline hydrochloride; pentosan polysulfate sodium; phenbutazone sodium glycerate; pirfenidone; piroxicam; piroxicam cinnamate; piroxicam olamine; pirprofen; prednazate; prednisolone; prifelone; prodolic acid; proquazone; proxazole; proxazole citrate; rimexolone; romazarit; salcolex; salnacedin; salsalate; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triamcinelone; triclonide; triflumidate; zidometacin; zomepirac sodium or combinations thereof.

Anti-inflammatory agents include steroidal agents or glucocorticosteroids. Phospholipase A2 ("PLA2") is a lipolytic enzyme that has been implicated as a possible mediator of inflammation. Specifically, PLA2 hydrolyses the 2-acyl position of glycerophospholipids, liberating free-fatty acids, mainly arachidonic acid. Subsequently, it is believed that arachidonic acid is converted into a variety of proinflammatory eicosanoids. Glucocorticosteroids are known to stop or reduce the suggested mechanisms of inflammation that involves the activation of the arachidonic acid cascade, which results in the liberation of a variety of proinflammatory eicosanoids by inducing lipocortin that inhibits PLA2. This provides a significant advantage over non-steroidal anti-inflammatory agents that enter the cascade much later.

Suitable glucocorticosteroids include, but are not limited to, alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluorometholone acetate, flurandrenolide, halcinonide, medrysone; methylprednisone suleptanate, pamidronate, paramethasone, prednisolone, nilutamide, triamcinelone, or combinations thereof.

Dexamethasone is of particular interest for use as an anti-inflammatory to treat orofacial diseases. Besides its anti-inflammatory property, dexamethasone can be delivered to up-regulate certain enzyme activities. Specifically dexamethasone can be used to increase or up-regulate alkaline phosphotase activity in regenerating human periodontal cells.

Exemplary anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol;

chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexl; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, and combinations thereof. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

Exemplary analgesics include, but are not limited to, acetaminophen; alfentanil hydrochloride; aminobenzoate potassium; aminobenzoate sodium; anidoxime; anileridine; anileridine hydrochloride; anilopam hydrochloride; anirolac; antipyrine; aspirin; benoxaprofen; benzydamine hydrochloride; bicifadine hydrochloride; brifentanil hydrochloride; bromadoline maleate; bromfenac sodium; buprenorphine hydrochloride; butacetin; butixirate; butorphanol; butorphanol tartrate; carbamazepine; carbaspirin calcium; carbiphene hydrochloride; carfentanil citrate; ciprefadol succinate; ciramadol; ciramadol hydrochloride; clonixeril; clonixin; codeine; codeine phosphate; codeine sulfate; conorphone hydrochloride; cyclazocine; dexoxadrol hydrochloride; dexpemedolac; dezocine; diflunisal; dihydrocodeine bitartrate; dimefadane; dipyrone; doxpicomine hydrochloride; drinidene; enadoline hydrochloride; epirizole; ergotamine tartrate; ethoxazene hydrochloride; etofenamate; eugenol; fenoprofen; fenoprofen calcium; fentanyl citrate; floctafenine; flufenisal; flunixin; flunixin meglumine; flupirtine maleate; fluproquazone; fluradoline hydrochloride; flurbiprofen; hydromorphone hydrochloride; ibufenac; indoprofen; ketazocine; ketorfanol; ketorolac and ketorolac tromethamine; letimide hydrochloride; levomethadyl acetate; levomethadyl acetate hydrochloride; levonantradol hydrochloride; levorphanol tartrate; lofemizole hydrochloride; lofentanil oxalate; lorcinadol; lomoxicam; magnesium salicylate; mefenamic acid; menabitan hydrochloride; meperidine hydrochloride; meptazinol hydrochloride; methadone hydrochloride; methadyl acetate; methopholine; methotrimeprazine; metkephamid acetate; mimbane hydrochloride; mirfentanil hydrochloride; molinazone; morphine sulfate; moxazocine; nabitan hydrochloride; nalbuphine hydrochloride; nalmexone hydrochloride; namoxyrate; nantradol hydrochloride; naproxen; naproxen sodium; naproxol; nefopam hydrochloride; nexeridine hydrochloride; noracymethadol hydrochloride; ocfentanil hydrochloride; octazamide; olvanil; oxetorone fumarate; oxycodone; oxycodone hydrochloride; oxycodone terephthalate; oxymorphone hydrochloride; pemedolac; pentamorphone; pentazocine; pentazocine hydrochloride; pentazocine lactate; phenazopyridine hydrochloride; phenyramidol hydrochloride; picenadol hydrochloride; pinadoline; pirfenidone; piroxicam olamine; pravadoline maleate; prodilidine hydrochloride; profadol hydrochloride; propiram fumarate; propoxyphene hydrochloride; propoxyphene napsylate; proxazole; proxazole citrate; proxorphan tartrate; pyrroliphene hydrochloride; remifentanil hydrochloride; salcolex; salethamide maleate; salicylamide; salicylate meglumine; salsalate; sodium salicylate; spiradoline mesylate; sufentanil; sufentanil citrate; talmetacin; talniflumate; talosalate; tazadolene succinate; tebufelone; tetrydamine; tifurac sodium; tilidine hydrochloride; tiopinac; tonazocine mesylate; tramadol hydrochloride; trefentanil hydrochloride; trolamine; veradoline hydrochloride; verilopam hydrochloride; volazocine; xorphanol mesylate; xylazine hydrochloride; zenazocine mesylate; zomepirac sodium; zucapsaicin or combinations thereof.

Exemplary anesthetics include by way of example and not limitation, aliflurane; benoxinate hydrochloride; benzocaine; biphenamine hydrochloride; bupivacaine hydrochloride; butamben; butamben picrate; chloroprocaine hydrochloride; cocaine; cocaine hydrochloride; cyclopropane; desflurane; dexivacaine; diamocaine cyclamate; dibucaine; dibucaine hydrochloride; dyclonine hydrochloride; enflurane; ether; ethyl chloride; etidocaine; etoxadrol hydrochloride; euprocin hydrochloride; fluroxene; halothane; isobutamben; isoflurane; ketamine hydrochloride; levoxadrol hydrochloride; lidocaine; lidocaine hydrochloride; mepivacaine hydrochloride; methohexital sodium; methoxyflurane; midazolam hydrochloride; midazolam maleate; minaxolone; nitrous oxide; norflurane; octodrine; oxethazaine; phencyclidine hydrochloride; pramoxine hydrochloride; prilocaine hydrochloride; procaine hydrochloride; propanidid; proparacaine hydrochloride; propofol; propoxycaine hydrochloride; pyrrocaine; risocaine; rodocaine; roflurane; salicyl alcohol; sevoflurane; teflurane; tetracaine; tetracaine hydrochloride; thiamylal; thiamylal sodium; thiopental sodium; tiletamine hydrochloride; zolamine hydrochloride; or combinations thereof.

The porous material can be saturated with one or more analgesics that can anesthetize the patients tooth and/or soft tissue area before the dental procedure is performed. In this way, the patient can place the oral appliance inside the oral cavity and the pre-filled oral appliance and porous material will numb the particular site. When the patient visits the dental professional, little delay will occur waiting for the area to numb. In this way, fast efficient dental procedures (e.g., tooth fillings, tooth extractions, root canal, dental cleanings, etc.) can be performed without delay to the dental provider or patient.

The porous material may contain one or more antineoplastic agents to treat cancer. Exemplary antineoplastic agents include by way of example and not limitation, acivicin; aclarubicin; acodazole hydrochloride; acrqnine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; ellomithine hydrochloride; elsamitrucin; enloplatin; enpromate; epipropidine; epirubicin hydrochloride; erbulozole; esorubicin hydrochloride; estramustine; estramustine phosphate sodium; etanidazole; ethiodized oil 1 131; etoposide; etoposide phosphate; etoprine; fadrozole hydrochloride; fazarabine; fenretinide; floxuridine; fludarabine phosphate; fluorouracil; flurocitabine; fosquidone; fostriecin sodium; genicitabine; gemcitabine hydrochloride; gold Au 198; hydroxyurea; idarubicin hydrochloride; ifosfamide; ilmofosine; interferon alpha-2a; interferon alpha-2b; interferon .alpha n1; interferon alpha n3; interferon beta Ia; interferon gamma Ib; iproplatin; irinotecan hydrochloride; lanreotide acetate; letrozole; leucovorin in combination with fluorouracil or methotrexate; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride Sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; or combinations thereof.

The porous material may contain one or more oral care medicaments that, in various embodiments, provide a benefit to the patient, without detriment to the oral surface to which it is applied. Examples of the oral conditions these medicaments address include, but, are not limited to, appearance to the teeth, whitening, stain bleaching, stain removal, plaque removal, tartar removal, cavity prevention and treatment, tooth recalcification, oral infections, inflamed and/or bleeding gums, mucosal wounds, lesions, ulcers, aphthous ulcers, cold sores, tooth abscesses, gingivitis, periodontal disease, xerostomia, post-surgical dressings and the elimination of mouth malodor.

For example, the tight fit of the oral appliance further forces the medicament out of the porous material to pool at the gingival margin but also causes to compress it and force it into the gingival sulcus and into the periodontal pockets. This is precisely where active periodontal disease is and where the medicament will be delivered. It is also an area with tremendous capillary blood flow and absorption. Thus, if desired, a medicament can be used that can provide systemic treatment (e.g., hypertension medication, diabetes medication, asthma medication, etc.).

Patients undergoing head and neck radiation treatment for cancer often suffer from high incidences of dental caries because of xerostomia (dry mouth). Xerostomia may also be caused by salivary gland disease, various medications and other causes. The oral appliance, in various embodiments, allows the patient to self administer a wide variety of medicaments comfortably, painlessly and in the convenience of their own home.

In various embodiments, suitable oral care medicaments include any material that is generally considered safe for use in the oral cavity and that provides changes to the overall appearance and/or health of the oral cavity. The level of oral care medicament is generally, unless specifically noted, from about 0.01% to about 50%, or from about 0.1% to about 20%, or from about 0.5% to about 10% or from about 1% to about 7%, by weight of the composition.

The porous material may comprise a safe and effective amount of one or more whitening agents (e.g., bleaching agents, abrasive agents). Generally the level of the bleaching agent is dependent on the available oxygen or chlorine respectively that the molecule is capable of providing to bleach the stain. The bleaching agent may be present at levels from about 0.1% to about 20%, in another embodiment from about 0.5% to about 9% and in another embodiment from about 3% to about 8%, and in yet another embodiment from about 4% to about 6%, by weight of the bleaching agent composition.

Typical bleaching agents suitable for use in the present application, include but are not limited to, peroxides, metal chlorites, perborates, percarbonates, peroxyacids, persulfates, compounds that form the preceding compounds in situ, and combinations thereof. Suitable peroxide compounds include hydrogen peroxide, urea peroxide, calcium peroxide, carbamide peroxide, and mixtures thereof. In one embodiment the bleaching agent is carbamide peroxide. Suitable metal chlorites include calcium chlorite, barium chlorite, magnesium chlorite, lithium chlorite, sodium chlorite, potassium chlorite, and mixtures thereof. Additional bleaching agents also include hypochlorite and chlorine dioxide. In one embodiment the bleaching agent is selected from sodium chlorite, peroxide, sodium percarbonate, oxones, and mixtures thereof. The starting bleach agent can be aqueous or solid material.

The porous material may comprise a safe and effective amount of an anticaries agent or mixtures thereof. In various embodiments, the anticaries agent can comprise xylitol, a fluoride ion source, and mixtures thereof. The fluoride ion source provides free fluoride ions during the use. Examples of fluoride ion sources, include, but are not limited to, sodium fluoride, stannous fluoride, indium fluoride, organic fluorides such as amine fluorides, and sodium monofluorophosphate or combination thereof. In various embodiments, the medicament provides from about 50 ppm to 10,000 ppm, or from about 100 to 3000 ppm of fluoride ions that contact tooth surfaces.

In various embodiments, the porous material may comprise a safe and effective amount of at least one anticalculus agent. This amount is generally from about 0.01% to about 40% by weight of the composition, in another embodiment from about 0.1% to about 25%, and in yet another embodiment from about 4.5% to about 20%, and in yet another embodiment from about 5% to about 15%, by weight of the composition. The anticalculus agent should also be compatible with the other components of the composition.

The anticalculus agent can contain polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. In another embodiment the anticalculus agent is a pyrophosphate, polyphosphate, and mixtures thereof.

In various embodiments, the porous material may comprise a safe and effective amount of at least one selective H-2 antagonist. Selective H-2 antagonists include, but are not limited to, cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408, burimamide, metiamide or combination thereof.

In various embodiments, the porous material may comprise a safe and effective amount of at least one nutrient that may improve the condition of the oral cavity and can be included in the porous material. Nutrients include minerals, vitamins, oral nutritional supplements, enteral nutritional supplements, and mixtures thereof. Minerals include, but are not limited to, calcium, phosphorus, fluoride, zinc, manganese, potassium and mixtures thereof.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof.

Oral nutritional supplements may also be included in the porous material. Oral nutritional supplements include amino acids, lipotropics, fish oil, and mixtures thereof. Amino acids include, but, are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid. Antioxidants may be included such as, for example, Vitamin E, ascorbic acid, Uric acid, carotenoids, Vitamin A, flavonoids and polyphenols, herbal antioxidants, melatonin, aminoindoles, lipoic acids and mixtures thereof.

Enteral nutritional supplements include, but, are not limited to protein products, glucose polymers, corn oil, safflower oil, medium chain triglycerides, flax seed oil. Anti-pain or desensitizing agents can also be included in or on the porous material. Such agents may include, but are not limited to, strontium chloride, potassium nitrate, natural herbs such as gall nut, Asarum, Cubebin, Galanga, scutellaria, Liangmianzhen, Baizhi, etc.

The porous material may contain one or more herbal products that occur in nature or come from plants. Some herbal medicaments include, but are not limited to, chondroitin sulfate, echinacea, ephedra (also called ma huang), garlic, ginkgo biloba, ginseng, glucosamine, kava, melatonin, phytoestrogens (such as black cohosh, dong quai and soy), saw palmetto, bee pollen, St. John's wort, or a combination thereof.

Apart from the active medicament, the porous material may optionally contain bulking agents, disintegrants, binders and lubricants, and excipients, which have no decisive effect on the delivery of active substances. Examples are, inter alia, bentonite (alumina silica hydrate), silica, cellulose (normally microcrystalline cellulose) or cellulose derivatives, for example methylcellulose, sodium carboxymethylcellulose, sugars such as lactose, starches, for example maize starch or derivatives thereof, for example sodium carboxymethylstarch, starch paste, phosphoric acid salts, for example di- or tricalcium phosphate, gelatin, stearic acid or suitable salts thereof, for example magnesium stearate or calcium stearate, talc, colloidal silica and similar ancillary substances.

Methods

In an exemplary embodiment, a method of delivering a medicament to at least a portion of teeth and/or soft tissue areas inside a mouth is provided, the method comprising: providing an oral appliance comprising an interior surface and a porous material disposed on at least the portion of the interior surface of the oral appliance and containing a medicament, the interior surface being formed to fit contours of at least the portion of the teeth and/or soft tissue areas inside the mouth and being capable of holding the porous material in contact with at least the portion of the teeth and/or soft tissue areas inside the mouth; and covering at least the portion of the teeth and/or soft tissue areas inside the mouth with the oral appliance supporting the porous material so that the porous material contacts at least the portion of the teeth and/or soft tissue areas inside the mouth to deliver the medicament.

The oral appliance can be used for treatment of diseases or conditions requiring therapy including whitening teeth. Treating or treatment of a disease refers to executing a protocol, which may include administering one or more oral appliance to a human patient or the patient may self-administer the oral appliance, in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes delivery where one or more medicaments contact the tooth and/or soft tissue areas, for example, the gingival margin of the mouth or a region of the inside of the mouth, or in close proximity thereto. "Targeted delivery" includes delivery of one or more medicaments at the target site as needed for treatment of the disease or condition including cosmetic applications (e.g., whitening teeth, removing stains, etc.).

The oral appliance may be disposable and sterilizable. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment. Other methods may also be used to sterilize one or more components of the oral appliance, including, but not limited to, E-beam radiation, gamma radiation, gas sterilization, such as, for example, with ethylene oxide or steam sterilization.

In various embodiments, a kit is provided which may include additional parts along with one or more oral appliances combined together. The kit may include the oral appliance and/or porous material combined or separated in a first compartment. A second compartment may include the additional porous materials or serial treatments of the oral appliance with different doses of one or more medicament designed to be used once and then disposed of, and other material needed to use the appliance. A third compartment may include gloves, drapes, dressings, plaque indicator swabs, and other procedural supplies, as well as an instruction booklet. Each oral appliance may be separately packaged in a plastic pouch that is sterilized. A cover of the kit may include illustrations of how to use the oral appliance and a clear plastic cover may be placed over the compartments to maintain sterility. These kits may be easily sent via mail to the patient and/or dental care professional.

The oral appliance may be used for localized and/or targeted delivery of the medicament to a patient to treat a disease or condition. Examples of diseases or conditions include, but, are not limited to, whitening, stain bleaching, stain removal, plaque removal, tartar removal, cavity prevention and treatment, tooth recalcification, oral infections, inflamed and/or bleeding gums, mucosal wounds, lesions, ulcers, aphthous ulcers, cold sores, tooth abscesses, gingivitis, periodontal disease, xerostomia and the elimination of mouth malodor. Some systemic diseases or conditions include, but are not limited to, hypertension, TMJ, migraines, GI ulcers, cardiac conditions, diabetes, neoplastic diseases, oral dermatologic diseases (e.g., lichen planus), hypothyroidism, hyperthyroidism, arthritis, or the like or combinations thereof.

Computer Implemented System

In various embodiments, a computer readable storage medium is provided for storing instructions that, when executed by a computer, cause the computer to create a treatment plan for delivering a medicament to at least a portion of the teeth and/or soft tissue areas inside the mouth, the computer readable storage medium receives an initial digital data set representing at least a portion of the teeth and/or soft tissue areas inside the mouth from scanning at least the portion of the teeth and/or soft tissue areas inside the mouth or a physical model or impression thereof; stores the initial digital data set in a database; generates a series of treatment plans to deliver the medicament to at least a portion of the teeth and/or soft tissue areas inside the mouth based on the stored initial digital data set, and constructing a series of oral appliances, via cad-cam technology, based on the stored initial digital data set, each appliance capable of delivering a medicament to at least a portion of the teeth and/or soft tissue areas inside the mouth.

In various embodiments, a computer-implemented method is provided for creating a treatment plan for delivering a medicament to at least a portion of the teeth and/or soft tissue areas inside the mouth, the computer-implemented method comprising: receiving an initial digital data set representing at least a portion of the teeth and/or soft tissue areas inside the mouth by scanning at least the portion of the teeth and/or soft tissue areas inside the mouth or a physical model or impression thereof; storing the initial digital data set in a database; generating a series of treatment plans to deliver the medicament to at least a portion of the teeth and/or soft tissue areas inside the mouth based on the stored initial digital data set, and constructing a series of oral appliances based on the stored initial digital data set, each appliance capable of delivering a medicament to at least a portion of the teeth and/or soft tissue areas inside the mouth.

In various embodiments, a computer based system is provided for creating a treatment plan for delivering a medicament to at least a portion of the teeth and/or soft tissue areas inside the mouth for storing and sharing treatment plan information among users, the system comprising: a user interface that displays options for a user to enter, view, and edit some or all of a treatment plan for delivering a medicament to at least a portion of the teeth and/or soft tissue areas inside the mouth, the computer based system comprising instructions for the computer to receive an initial digital data set representing at least a portion of the teeth and/or soft tissue areas inside the mouth by scanning at least the portion of the teeth and/or soft tissue areas inside the mouth or a physical model or impression thereof; storing the initial digital data set in a database; generating a series of treatment plans to deliver the medicament to at least a portion of the teeth and/or soft tissue areas inside the mouth based on the stored initial digital data set, and constructing a series of oral appliances, via cad-cam technology, based on the stored initial digital data set, each appliance capable of delivering a medicament to at least a portion of the teeth and/or soft tissue areas inside the mouth, wherein the treatment plan is available over a computer network to more than one user.

In various embodiments, the computer scan is used not only to generate one or more appliances, but also is used to generate one or more porous materials. The oral appliance can be fabricated manually or by any computer assisted manufacturing technology, such as for example, cad-cam technology, used to design, develop and optimize the design of the oral appliance.

Figure 7:
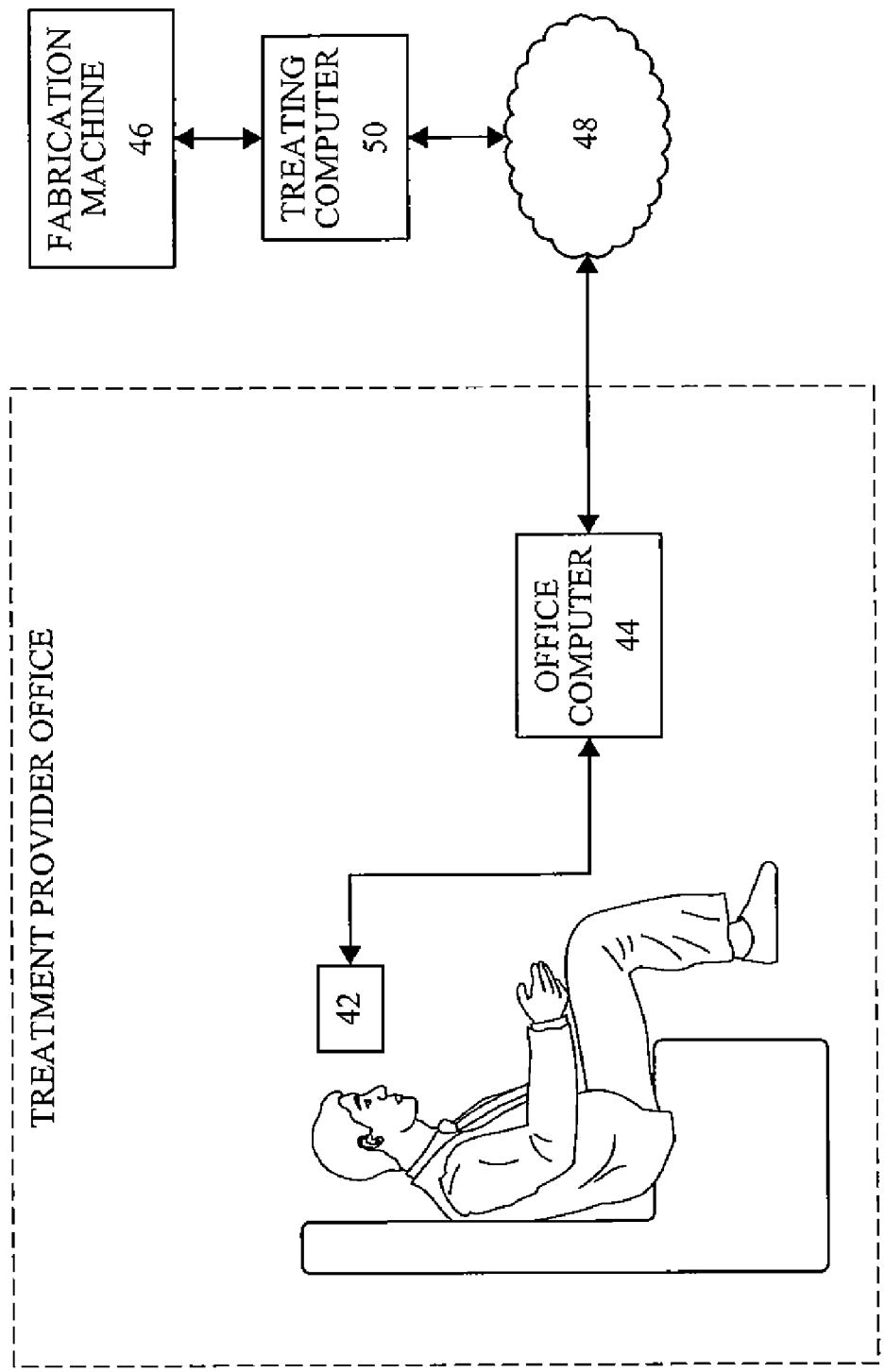
FIG. 7 illustrates an embodiment of the computer-implemented system for treating a patient at a treatment provider's office.

Referring to FIG. 7, it illustrates an embodiment of the computer-implemented system for treating a patient at a treatment provider's office. A scanner 42 is used to scan a patient. The scanner can be an MRI scanner, an X-Ray machine, or an intra-oral scanner, for example. In various embodiments, the scanner 42 can scan the patient's teeth, soft tissue, or both to obtain a digital data of the teeth and/or soft tissue areas inside the mouth to use to generate the appliance or the scanner can scan a conventional model or impression mould of the teeth and/or soft tissue areas inside the mouth to use the data to generate the appliance. The digital data can be stored in the office computer database 44 and can be accessible over the internet or network 48 by a treatment computer 50, where the authorized user (e.g., dentist, dental specialist, dental hygienist, oral surgeon, physician, surgeon, nurse, health care provider, etc.) can prescribe, design an appliance, change the prescription, approve it, reject it, and/or edit it. Once approved, the data can be sent to the fabrication machine (cad-cam) database 46 which can generate the oral appliance including the porous material based on the scanned and stored digital data in office computer 44 and/or treating computer 50.

In various embodiments, the scanner 42 is an intra-oral scanner, and data from the teeth and/or soft tissue areas scan is uploaded to an office computer 44 that, among others, generates a computer representation of the teeth and/or soft tissue areas inside the mouth of the patient. The office computer 44 sends the data via network 48 to the treating computer at the factory 50 to generate images of one or more appliances to treat the patient's teeth in accordance with the diagnosed condition or treatment plan. The oral appliance does not move teeth.

An authorized user can input, edit data and approve or prescribe a treatment plan based on the data displayed at the user interface of the office computer and/or treating computer. Authorized users may include at least one dentist or dental specialist, dental hygienist, oral surgeon, physician, surgeon, nurse, patient, health care provider, manufacturer, etc.).

The user interface may include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of a user with the system via user interface. The user interface may be directly coupled to database or directly coupled to a network server system via the internet. In accordance with one embodiment, one or more user interfaces are provided as part of (or in conjunction with) the illustrated systems to permit users to interact with the systems.

The user interface device may be implemented as a graphical user interface (GUI) containing a display or the like, or may be a link to other user input/output devices known in the art. Individual ones of a plurality of devices (e.g., network/stand-alone computers, personal digital assistants (PDAs), WebTV (or other Internet-only) terminals, set-top boxes, cellular/phones, screenphones, pagers, blackberry, peer/non-peer technologies, kiosks, or other known (wired or wireless) communication devices, etc.) may similarly be used to execute one or more computer programs (e.g., universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (e.g., the Internet).

The database is configured to be protected from access by unauthorized users (e.g., hackers, viruses, worms, spy ware, etc.). Although the computers may be shown or described herein as physically separated components (e.g., office computer 44, scanner 42, etc.), it should be readily apparent that the computer and/or databases as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general-purpose computer (or other processor-controlled device) executing a program stored on an article of manufacture (e.g., recording medium or other memory units) to produce the functionality referred to herein may be utilized to implement the illustrated embodiments.

Database may be any one or more of the known storage devices or systems (e.g., Random Access Memory (RAM), Read Only Memory (ROM), hard disk drive (HDD), floppy drive, zip drive, compact disk-ROM, DVD, bubble memory, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into centralized database, a tracking component for tracking information received and entered, a search component to search information in the database or other databases, a receiving component to receive a specific query from a user interface, and an accessing component to access centralized database. Receiving component is programmed for receiving a specific query from one of a plurality of users. The database may also include a processing component for searching and processing received queries against data storage device containing a variety of information collected by collection component.

In accordance with one embodiment, the data may be downloaded in one or more textual/graphical formats (e.g., RTF, PDF, TIFF, JPEG, etc.), or set for alternative delivery to one or more specified locations (e.g., via e-mail, fax, regular mail, courier, etc.) in any desired format (e.g., print, storage on electronic media and/or computer readable storage media such as CD-ROM, etc.). The user may view viewing the search results and underlying documents at the user interface, which allows viewing of one or more documents on the same display.

In one embodiment, the computer software can create a 2D or 3D digital image of the patient's oral cavity to allow the treatment provider to review and discuss the proposed treatment with the patient. In another embodiment, the software can process the scanned data and provide the user/operator with useful data and tooth measurements (e.g. arch width, arch length, tooth size, angulations, sulcus size, etc.) to assist the user in fine-tuning the treatment plan. The computer can then provide the operator with options in staging the treatment plan from one stage to another stage, or it can completely generate all stages ranging from the initial to final desired stage. The staging can be done automatically.

Figure 8:
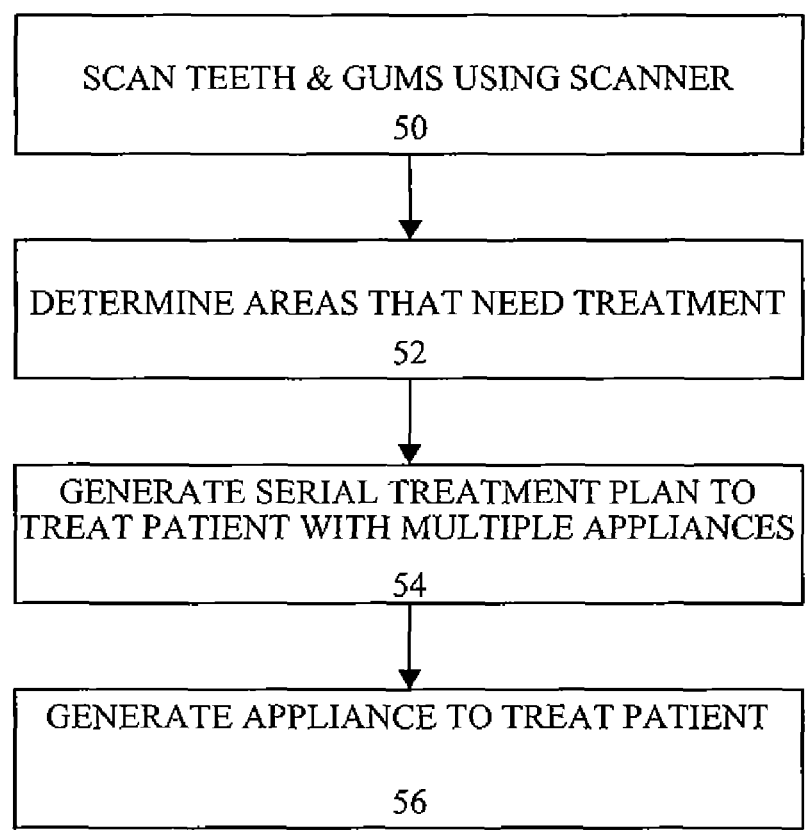
FIG. 8 is a flow chart illustrating an embodiment of the computer-implemented system for treating a patient at a treatment provider's office.

FIG. 8 is a flow chart illustrating an embodiment of the computer-implemented system for treating a patient at a treatment provider's office with multiple oral appliances. The process includes first digitally scanning the oral cavity of the patient 50 at the treatment provider's office and the digital image is reviewed and the areas that need treatment are determined 52 and stored on the database. The data is used to generate a treatment plan to treat the patient with multiple oral appliances 54 and to then generate multiple oral appliances 56.

Figure 9:
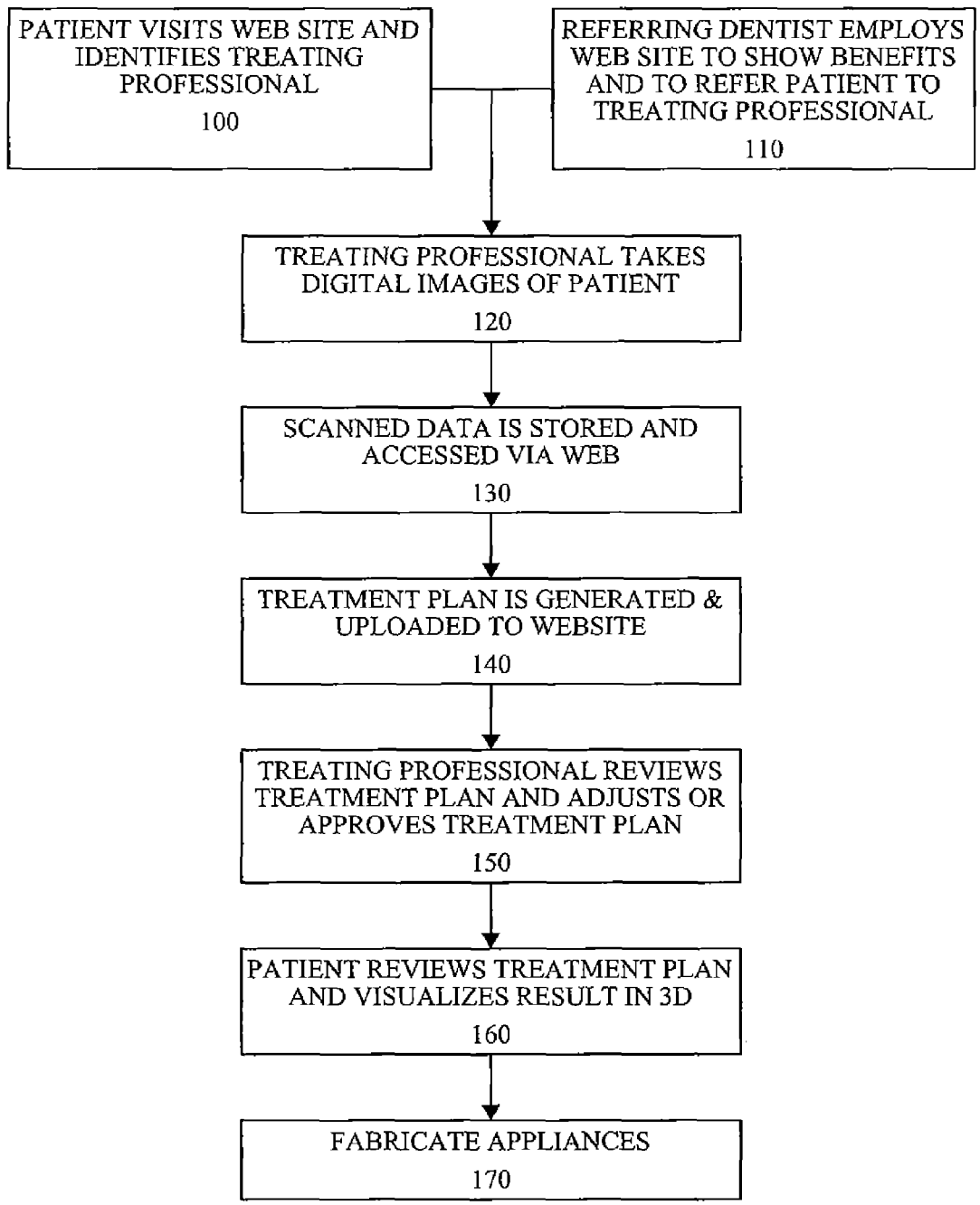
FIG. 9 is a flow chart illustrating an embodiment of the computer-implemented system employing a website user interface that allows a patient to select a particular treatment provider.

FIG. 9 illustrates an exemplary usage of the system via a patient-provider web interface. A prospective patient uses a computer 100 and visits the web site on the dental server 110. The patient identifies a treatment provider, who has received training in the methodology and is certified, and then schedules an appointment with the treatment provider 110. Alternatively, a referring dentist can refer the client to the treating professional. The referring dentist can visit the web site on the dental server and use one or more dental esthetic tools to show patients the potential benefits of the treatment.

During an initial examination, the treatment provider or an assistant takes a set of digital scans of the teeth and/or soft tissue areas 120, which is uploaded, to a secure, collaborative workspace on the dental server 130, which is accessible on the web 140. The workspace is shared with the referring dentist and the treatment plan can be reviewed and approved by one or more professionals 150. Next, the treatment provider generates a treatment visualization showing the patient's oral cavity and the proposed oral appliance 160. An oral appliance is generated upon approval and can be sent to the patient by mail or an appointment can be scheduled for the health care provider to instruct the patient in the use of the appliance and commence treatment.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An oral appliance for delivering a medicament to teeth and soft tissue areas inside a mouth, the oral appliance being custom fit to the mouth and comprising a non-porous exterior surface that prevents the medicament from being diluted by saliva and an interior surface having a porous material disposed on at least a portion of the interior surface of the oral appliance, the porous material comprising a sponge or foam pre-filled with one or more doses of the medicament and the interior surface being custom fit and formed to fit contours of the teeth and soft tissue areas inside the mouth and being capable of supporting and holding the porous material to deliver the medicament, wherein the interior surface is formed from a hard thermoplastic material molded to correspond to the contours of the teeth and soft tissue areas inside the mouth and the porous material is supported and held within a cargo area of the interior surface of the thermoplastic material of the oral appliance and the cargo area is continuous and is configured to extend adjacent to the gums and all the teeth and the sponge or foam is a single continuous piece disposed in the cargo area and is configured to extend, along a length of the sponge or foam, from buccal surfaces of the teeth and surrounding gingival tissue, over occlusal surfaces of the teeth, over lingual surfaces of the teeth, and over adjacent gingival tissue on a lingual side of the teeth and the sponge or foam has a surface that corresponds to the cargo area and the sponge or foam has a portion having increased thickness, extending in a direction transverse to the length of the sponge or foam, that is complementary to and locks into the cargo area.

2. An oral appliance according to claim 1, wherein the soft tissue areas inside the mouth include muco-buccal folds, hard palate, soft palate, lining mucosa, attached gingival tissue, and mouth floor tissue.

3. An oral appliance according to claim 1, wherein the medicament is configured to be delivered to the buccal surfaces, surrounding gingival tissue, occlusal surfaces, the lingual surfaces, and adjacent gingival tissue on the lingual side of the teeth.

4. An oral appliance according to claim 1, wherein the medicament is configured to be delivered to the soft tissue and teeth at or near a gingival margin or sulcus.

5. An oral appliance according to claim 1, wherein at least one of: (i) the porous material has a depth of from about 1 mm to about 5 mm; (ii) the porous material has a width of from about 1 mm to about 10 mm; or (iii) the oral appliance has a thickness of from about 0.06 inches to about 0.2 inches.

6. An oral appliance according to claim 1, wherein the porous material is configured to deliver the medicament to the gingival margin.

7. An oral appliance according to claim 1, wherein the porous material is configured to deliver the medicament to: (i) a muco-gingival junction; (ii) at least 2 mm to 5 mm buccally beyond a gingival margin; or (iii) at least 2 mm to 5 mm lingually beyond a gingival margin.

8. An oral appliance according to claim 1, wherein the porous material is configured to deliver at least one of (i) a bolus dose of the medicament; (ii) a single dose of the medicament; or (iii) multiple doses of the medicament.

9. An oral appliance according to claim 1, wherein the sponge or foam comprises a cushion zone.

10. An oral appliance according to claim 1, wherein the medicament comprises at least one analgesic, whitening agent, breath freshener, anti-inflammatory, anticalculus agent, antimicrobial, anesthetic, muscle relaxant, selective H-2 antagonists, anticaries agent, nutrient, vitamin, mineral, herbal product, or mixtures thereof.

11. An oral appliance according to claim 1, wherein the oral appliance is constructed from a digital data set.

12. An oral appliance according to claim 1, wherein the oral appliance is constructed from a digital data set or a physical model thereof representing all of the teeth and soft tissue areas inside the mouth.

13. An oral appliance according to claim 1, wherein the porous material is saturated with liquid medicament for optimum flow to deliver the medicament.

14. An oral appliance for delivering a medicament according to claim 1, wherein the sponge or foam is compressible to release the medicament.

15. An oral appliance according to claim 1, wherein the oral appliance is configured to deliver medicament to the gums.

16. A method of delivering medicament to teeth and soft tissue areas inside a mouth, the method comprising:
providing an oral appliance comprising a non-porous exterior surface that prevents medicament from being diluted by saliva and an interior surface and a porous material disposed on at least a portion of the interior surface of the oral appliance and, the porous material comprising a sponge or foam pre-filled with one or more doses of medicament, the interior surface formed to fit contours of the teeth and soft tissue areas inside the mouth and being capable of holding the porous material; and
covering the teeth and soft tissue areas inside the mouth with the oral appliance holding the porous material to deliver the medicament, wherein the interior surface is formed from a hard thermoplastic material molded to correspond to the contours of the teeth and soft tissue areas inside the mouth and the porous material is supported and held within a cargo area of the interior surface of the thermoplastic material of the oral appliance and the cargo area is continuous and extends adjacent to the gums and all the teeth and the sponge or foam is a single continuous piece disposed in the cargo area and extends, along a length of the sponge or foam, from buccal surfaces of the teeth and surrounding gingival tissue, over occlusal surfaces of the teeth, over lingual surfaces of the teeth, and over adjacent gingival tissue on a lingual side of the teeth and the sponge or foam has a surface that corresponds to the cargo area and the sponge or foam has a portion having increased thickness, extending in a direction transverse to the length of the sponge or foam, that is complementary to and locks into the cargo area.

17. A method according to claim 16, further comprising maintaining inside the mouth for a sufficient time to allow a therapeutically effective amount of the medicament to be delivered.

18. A method according to claim 16, wherein the medicament comprises at least one analgesic, whitening agent, anti-inflammatory, anticalculus agent, antimicrobial, anesthetic, selective H-2 antagonists, anticaries agent, nutrient, vitamin, mineral, herbal product, or mixtures thereof.

19. A method according to claim 16, wherein the medicament comprises at least one systemic drug.

20. A method of delivering medicament to teeth and soft tissues areas inside a mouth, the method comprising:
providing an oral appliance, the oral appliance being custom fit by a dental provider to the mouth of a patient, the oral appliance comprising a non-porous exterior surface that prevents medicament from being diluted by saliva and an interior surface and a porous material disposed on at least a portion of the interior surface of the oral appliance, the porous material comprising a custom fit sponge or foam prescribed by the dental provider and pre-filled with one or more doses of medicament, the interior surface being formed to fit contours of the teeth and soft tissue areas inside the mouth and being capable of holding the porous material; and
covering the teeth and soft tissue areas inside the mouth with the oral appliance to deliver the medicament, the porous material being a single continuous piece disposed in a cargo area and extends, along a length of the sponge or foam, from buccal surfaces of the teeth and surrounding gingival tissue, over occlusal surfaces of the teeth, over lingual surfaces of the teeth, and over adjacent gingival tissue on a lingual side of the teeth, wherein the interior surface comprises a hard thermoplastic material molded to correspond to the contours of the teeth and soft tissue areas inside the mouth and the porous material is supported and held within the cargo area of the interior surface of the thermoplastic material of the oral appliance and the sponge or foam has a surface that corresponds to the cargo area and the sponge or foam has a portion having increased thickness, extending in a direction transverse to the length of the sponge or foam, that is complementary to and locks into the cargo area.

21. A method of delivering medicament according to claim 20, wherein the dental provider is a dentist.

22. An oral appliance for delivering a medicament to all teeth inside a mouth, the oral appliance comprising a non-porous exterior surface that prevents the medicament from being diluted by saliva and an interior surface having a porous material disposed on at least a portion of the interior surface of the oral appliance, the porous material comprising a sponge or foam pre-filled with one or more doses of the medicament and the interior surface being capable of supporting and holding the porous material in contact with all the teeth inside the mouth to deliver the medicament, wherein the interior surface is formed from a hard thermoplastic material molded to correspond to the contours of at least all the teeth and the porous material is supported and held within a cargo area of the interior surface of the thermoplastic material of the oral appliance and the cargo area is continuous and is configured to extend adjacent to all the teeth and the sponge or foam is a single continuous piece disposed in the cargo area and is configured to extend, along a length of the sponge or foam, over the front, back and occlusal surfaces of all the teeth and the sponge or foam has a surface that corresponds to the cargo area and the sponge or foam has a portion having increased thickness, extending in a direction transverse to the length of the sponge or foam, that is complementary to and locks into the cargo area.

23. An oral appliance according to claim 22, wherein the porous material is configured to deliver at least one of (i) a bolus dose of the medicament; (ii) a single dose of the medicament; or (iii) multiple doses of the medicament.

24. An oral appliance for delivering a medicament to all the teeth and adjacent buccal and lingual tissue inside a mouth, the oral appliance comprising a non-porous exterior surface that prevents the medicament from being diluted by saliva and an interior surface having a porous material disposed on at least a portion of the interior surface of the oral appliance, the porous material comprising a sponge or foam pre-filled with one or more doses of the medicament and the interior surface being capable of supporting and holding the porous material in contact with all the teeth and adjacent buccal and lingual tissue inside the mouth to deliver the medicament, wherein the interior surface is formed from a hard thermoplastic material molded to correspond to the contours of all the teeth and adjacent buccal and lingual tissue inside the mouth and the porous material is supported and held within a cargo area of the interior surface of the thermoplastic material of the oral appliance and the cargo area is continuous and is configured to extend adjacent to all the teeth and adjacent buccal and lingual tissue and the porous material is a single continuous piece disposed in the cargo area and is configured to cover all the teeth and is configured to extend, along a length of the sponge or foam, to adjacent buccal and lingual tissue across occlusal surfaces of all the teeth and the sponge or foam has a surface that corresponds to the cargo area and the sponge or foam has a portion having increased thickness, extending in a direction transverse to the length of the sponge or foam, that is complementary to and locks into the cargo area.

25. An oral appliance according to claim 24, wherein the porous material is configured to deliver at least one of (i) a bolus dose of the medicament; (ii) a single dose of the medicament; or (iii) multiple doses of the medicament.

* * * * *